(12) United States Patent
Ao et al.

(10) Patent No.: US 9,409,845 B2
(45) Date of Patent: Aug. 9, 2016

(54) ALPHA-(3,5-DIMETHOXYBENZYLIDENE)-ALPHA'-HYDROCARBYL METHYLENE CYCLIC KETONE AND PREPARATION METHOD THEREOF

(71) Applicant: PHARMAXYN LABORATORIES LTD., Wuxi (CN)

(72) Inventors: Guizhen Ao, Wuxi (CN); Jihua Nie, Wuxi (CN); Huanqiu Li, Wuxi (CN); Lingxuan Mo, Wuxi (CN); Lei Chen, Wuxi (CN); Heng Song, Wuxi (CN); Shaohua Chen, Wuxi (CN)

(73) Assignee: PHARMAXYN LABORATORIES LTD., Wuxi (CN)

( * ) Notice: Subject to any disclaimer, the term of this patent is extended or adjusted under 35 U.S.C. 154(b) by 0 days.

(21) Appl. No.: 14/723,785

(22) Filed: May 28, 2015

(65) Prior Publication Data

US 2015/0259271 A1 Sep. 17, 2015

Related U.S. Application Data

(63) Continuation of application No. PCT/CN2013/088012, filed on Nov. 28, 2013.

(30) Foreign Application Priority Data

Nov. 28, 2012 (CN) .......................... 2012 1 0496017

(51) Int. Cl.
| | |
|---|---|
| C07C 45/00 | (2006.01) |
| A61K 31/00 | (2006.01) |
| C07C 49/753 | (2006.01) |
| C07C 317/24 | (2006.01) |
| C07C 225/22 | (2006.01) |
| C07C 45/45 | (2006.01) |

(52) U.S. Cl.
CPC ............... *C07C 49/753* (2013.01); *C07C 45/45* (2013.01); *C07C 225/22* (2013.01); *C07C 317/24* (2013.01); *C07C 2101/14* (2013.01)

(58) Field of Classification Search
CPC .............................. C07C 45/45; A61K 31/122
USPC ............................ 568/329, 330; 514/683, 684
See application file for complete search history.

(56) References Cited

U.S. PATENT DOCUMENTS 6,777,447 B2 * 8/2004 Reksohadiprodjo .... C07C 45/74
514/677

OTHER PUBLICATIONS

Yadev et al. Synthesis and cytotoxic potential of heterocyclic cyclohexanone analogues of curcumin. Bioorganic & Medicinal Chemistry, vol. 18, 2010, 6701-6707.*

Gafner et al. Biologic evaluation of curcumin and structural derivatives in cancer chemoprevention and model systems. Phytochemistry, vol. 65, 2004, 2849-2859.*

* cited by examiner

*Primary Examiner* — Sikarl Witherspoon
(74) *Attorney, Agent, or Firm* — Flener IP Law; Zareefa B. Flener

(57) ABSTRACT

The present invention discloses a α-(3,5-dimethoxybenzylidene)-α'-hydrocarbyl methylene cyclic ketone with the following formula:

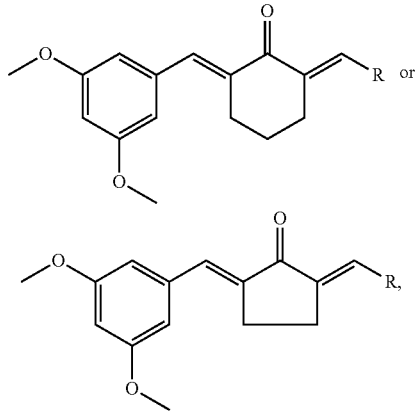

wherein R is aryl or alkyl, its preparation method is: the cyclic ketone blended with morpholine are subjected to azeotropic dehydration to give enamine, the enamine is condensed with 3,5-dimethoxybenzaldehyde and then condensed with alkyl or aryl formaldehyde under acidic or basic conditions to give the product, the present invention further discloses an antitumor agent comprising α-(3,5-dimethoxybenzylidene)-α'-hydrocarbyl methylene cyclic ketone or medically acceptable salts and pharmaceutically acceptable carriers thereof. Through the above, the present invention providesα-(3,5-dimethoxybenzylidene)-α'-hydrocarbyl methylene cyclic ketone and preparation method thereof, the said compound is a high activity antitumor agent obtained by piecing and modifying the formulas of natural anti-tumor active ingredient resveratrol and curcumin, which has a good inhibitory effect on epidermal growth factor receptor.

8 Claims, No Drawings

ALPHA-(3,5-DIMETHOXYBENZYLIDENE)-ALPHA'-HYDROCARBYL METHYLENE CYCLIC KETONE AND PREPARATION METHOD THEREOF

CROSS-REFERENCE TO RELATED APPLICATION

The application is a continuation of PCT/CN2013/088012 (filed on Nov. 28, 2013), which claims priority of CN patent application Ser. No. 201210496017.1 (filed on Nov. 28, 2012), the contents of which are incorporated herein by reference for all purposes.

FIELD OF THE INVENTION

The present invention is related to the field of antitumor agents, in particular to a α-(3,5-dimethoxybenzylidene)-α'-hydrocarbyl methylene cyclic ketone and preparation method thereof.

BACKGROUND OF THE INVENTION

Cancer has become one of major diseases which are increasingly common and threaten human life and the quality of life, and tumor has risen to No. 2 "killer" in the world after cardiovascular disease, but the lesions and metastasis of cancer cells as well as mechanism of action of drugs on cancer cells are still not clear. Now the treatment of cancer is still largely chemotherapy based on antitumor agent, but chemical drugs have toxic side effects, multi-drug resistance and other issues. Epidermal growth factor receptor (EGFR) inhibitors acting on related tumor cells can enhance tumor cell destruction and reduce the adverse effects on normal tissue cells and so on. These drugs have non-cytotoxicity, targeting, regulation and cell stabilizing effects, its toxicity and clinical manifestations are very different from commonly used cytotoxic drugs, there will be better effects when combined with conventional chemotherapy or radiotherapy.

Resveratrol is a natural polyphenolic compound, mainly from the rhizome extract of *Polygonum cuspidatum*, with a variety of biological effects, including the neuroprotective effect, cardiovascular protective effect, anti-inflammatory and anti-tumor effects, etc., which especially has important clinical value in inhibition of liver cancer, stomach cancer, leukemia, cervical cancer, esophageal cancer and other cancers. Resveratrol exhibits inhibition in the onset, promotion and development phases of cancer, making it apply to the field of chemoprevention and therapy of cancer.

Curcumin, extracted from rhizome of the ginger family plant turmeric, *curcuma zedoaria*, is an important active ingredient with strong pharmacological activity and broad indications, which has a variety of pharmacological effects including anti-inflammatory, anti-tumor, anti-angiogenic, anti-mutagenic, anti-bacterial, anti-viral, anti-oxidant and neuroprotectioneffects. The anti-tumor effect of curcumin includes in vitro growth inhibition and induction of apoptosis on a variety of tumor cells, and in vivo inhibition of tumorigenesis, but the properties of curcumin, e.g. low in vivo activity, little in vivo absorption less, fast metabolism and low bioavailability, greatly limit its application.

SUMMARY OF THE INVENTION

The present invention is mainly to solve the technical problems of providing the compound of α-(3,5-dimethoxybenzylidene)-α'-hydrocarbyl methylene cyclic ketone and preparation method thereof, which has anti-tumor effects.

To solve the above technical problems, one embodiment of the present invention is to provide α-(3,5-dimethoxybenzylidene)-α'-hydrocarbyl methylene cyclic ketone with formula:

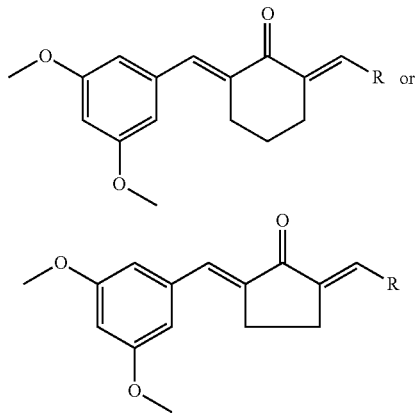

or its medically acceptable salt, wherein R is aryl or alkyl group.

In a preferred embodiment of the present invention, the formula of the aryl group is

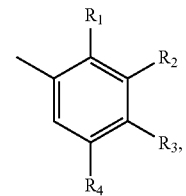

wherein $R_1$ is selected from hydrogen, hydroxy, halogen, amino, methylsulphonyl, alkoxy containing 1 to 4 carbon, alkyl, haloalkyl or alkylamino group, $R_2$ is selected from hydrogen, hydroxy, halogen, amino, methylsulphonyl, alkoxy containing 1 to 4 carbon, alkyl, haloalkyl or alkylamino group, $R_3$ is selected from hydrogen, hydroxy, halogen, amino, containing 1 to 4 carbon, alkoxy containing 1 to 4 carbon, alkyl, haloalkyl or alkylamino, $R_4$ is selected from hydrogen, hydroxy, halogen, amino, methylsulphonyl, alkoxy containing 1 to 4 carbon, alkyl, haloalkyl or alkylamino group; the alkyl group is preferred selected from alkyl containing 1 to 8 carbon.

The invention also provides a method of preparation of α-(3,5-dimethoxybenzyl-idene)-α'-hydrocarbyl methylene cyclic ketone, comprising the steps of: mix the cyclic ketone and morpholine and follow azeotropic dehydration to obtain enamine; the enamine and 3,5-dimethoxybenzaldehyde occur condensation reaction to obtain E-α-(3,5-dioxobenzylidene)-cyclic ketone; the condensation of E-α-(3,5-dioxobenzylidene)-cyclic ketone with alkyl or aryl formaldehyde under acidic or basic conditions affords α-(3,5-dimethoxybenzylidene)-α'-hydrocarbyl methylene cyclic ketone.

In a preferred embodiment of the invention, the cyclic ketone is selected from cyclohexanone or cyclopentanone.

The invention also provides an antitumor agent including α-(3,5-dimethoxybenzylidene)-α'-hydrocarbyl methylene cyclic ketone and pharmaceutically acceptable carriers.

The invention also provide an antitumor agent including medically acceptable salt of α-(3,5-dimethoxybenzylidene)-α'-hydrocarbyl methylene cyclic ketone and pharmaceutically acceptable carriers.

In a preferred embodiment of the present invention, said α-(3,5-dimethoxybenzylidene)-α'-hydrocarbyl methylene cyclic ketone accounts for 0.05 to 90% by weight of the anti-tumor agent.

In a preferred embodiment of the present invention, said α-(3,5-dimethoxybenzylidene)-α'-hydrocarbyl methylene cyclic ketone accounts for 15-60% by weight of the antitumor agent.

In a preferred embodiment of the invention, the carrier comprises solvent, diluent, tablet, capsule, dispersible powder, or granule.

The beneficial effects of the present invention are: according to the α-(3,5-dimethoxybenzyl-idene)-α'-hydrocarbyl methylene cyclic ketone of the present invention and preparation method thereof, the α-(3,5-dimethoxybenzylidene)-α'-hydrocarbyl methylene cyclic ketone is obtained by piecing together and modifying the formula of resveratrol and curcumin, which are the active ingredients of natural product, and the present invention gives a antitumor agent having a much more activity and inhibitory effect on epidermal growth factor receptor.

DETAILED DESCRIPTION OF THE INVENTION

The preferred embodiments of the present invention are illustrated in detail, so that the advantages and features of the present invention can be more readily understood by those skilled in the art, and thus the scope of the present invention is defined more clearly.

The present invention provides an α-(3,5-dimethoxybenzylidene)-α'-hydrocarbyl methylene cyclic ketone with general formula:

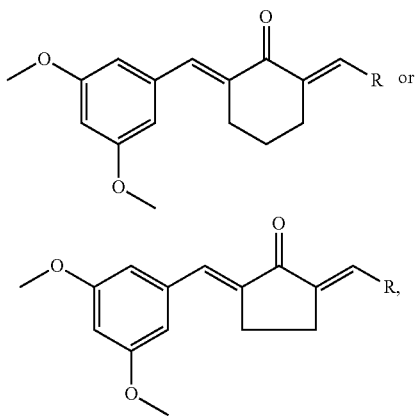

wherein R is an aryl group or an alkyl group, when the material is cyclohexanone, α' means 6-position of the general formula α-(3,5-dimethoxybenzylidene)-α'-hydrocarbyl methylene cyclic ketone is substituted, when the material is cyclohexanone, α' means 5-position of the general formula α-(3,5-dimethoxy-benzylidene)-α'-hydrocarbyl methylene cyclic ketone is substituted.

EXAMPLE 1

(1) 10.79 g (0.11 mol) of cyclohexanone and 10.4 g (0.12 mol) of morpholine were added to 20 mL benzene, refluxed azeotropically after a trap was equipped, when no water was generated, benzene and morpholine were evaporated under reduced pressure to give enamine. 6.54 g (0.043 mol) of enamine and 5.40 g (0.033 mol) of 3,5-dimethoxybenzaldehyde were added to 20 mL benzene, refluxed azeotropically after a trap was equipped until no water was generated in a total of 8 h, after cooling to room temperature, 6 mol/L hydrochloric acid was added slowly with stirring, and stirred at room temperature for 2 h, the benzene layer was separated, the aqueous layer was extracted with benzene layer, benzene layers were combined and dried over anhydrous sodium sulfate, after evaporating the solvent under reduced pressure and recrystallizing with petroleum ether and ethanol, E-2-(3,5-dioxobenzylidene)cyclohexanone was obtained as yellow needles, yield: 74%, mp 55.0~56.6. $^1$H-NMR: δ: 7.41 (s, 1H, =CH), 6.53 (d, 2H, J=2.0 Hz, ArH), 6.45 (t, 1H, J=2.0 Hz, ArH), 3.80 (s, 6H, OCH$_3$), 2.84 (dt, 2H, J=1.9, 6.5 Hz, CH$_2$), 2.54 (t, 2H, J=6.6 Hz, CH$_2$), 1.90 (m, 2H, CH$_2$), 1.78 (m, 2H, CH$_2$).

(2) 300 mg (1.22 mmol) of E-2-(3,5-dioxobenzylidene) cyclohexanone and 129 mg (124 μL, 1.22 mmol) of benzaldehyde were added to 10 mL 10% NaOH solution in ethanol, stirred at room temperature for 30 min to complete the reaction, 50 mL of water and 20 mL×3 ethyl acetate were added for extraction, after evaporating the solvent and drying over anhydrous sodium sulfate, 355 mg of (2E,6E)-2-(3,5-dimethoxy-benzylidene)-6-benzylidene cyclohexanone as pale yellow needles was obtained by column chromatography with ethyl acetate and petroleum ether in volume ratio of 15:1, yield: 87.2%, mp 90.2~91.0 $^1$H-NMR(400 MHz, CDCl$_3$):δ: 7.59~7.60 (m, 3H, =CH, ArH), 7.52 (s, 1H, =CH), 7.45 (t, 2H, 7.2 Hz, ArH), 7.37~7.40 (m, 1H, ArH), 6.75 (s, 2H, ArH), 6.51 (s, 1H, ArH), 3.83 (s, 6H, OCH$_3$), 3.11 (s, 4H, —CH$_2$); $^{13}$C-NMR (400 MHz, CDCl$_3$):δ=196.375, 160.962, 137.885, 137.707, 137.423, 135.940, 134.021, 133.964, 130.955, 129.595, 128.954, 108.879, 101.799, 55.557, 26.690, 26.658; HR-MS: Calcd. For C$_{21}$H$_{20}$O$_3$[M+H]$^+$: 321.1485, Found: 321.1475.

EXAMPLE 2

E-2-(3,5-dioxobenzylidene)-cyclohexanone and 3-chlorobenzaldehyde were as the starting materials, see Example 1 for preparation method. Compound (2E,6E)-2-(3,5-dimethoxybenzyl-idene)-6-(3-chloro benzylidene)cyclohexanone has melting point of 107.5~108.4, $^1$H-NMR(400 MHz, CDCl$_3$): δ: 7.72 (s, 1H, =CH), 7.70 (s, 1H, =CH), 7.43 (s, 1H, ArH), 7.33 (m, 3H, ArH), 6.61 (d, 2H, J=2.1 Hz, ArH), 6.47 (t, 1H, J=2.1 Hz, ArH), 3.82 (s, 6H, OCH$_3$), 2.92 (m, 4H, CH$_2$), 1.81 (quint, 2H, J=6.5 Hz, CH$_2$). $^{13}$C-NMR (400 MHz, CDCl$_3$): δ: 190.257, 160.841, 137.985, 137.876, 137.577, 137.541, 136.631, 135.558, 134.564, 130.172, 129.936, 128.795, 108.625, 101.106, 55.707, 28.762, 28.684, 23.117. HR-MS: Calcd. For C$_{22}$H$_{21}$ClO$_3$ [M+H]$^+$: 369.1252, Found: 369.1257.

EXAMPLE 3

E-2-(3,5-dioxobenzylidene)-cyclohexanone and 2-chlorobenzaldehyde were as the starting materials, see Example 1 for preparation method. Compound (2E,6E)-2-(3,5-dimethoxybenzyl-idene)-6-(2-chlorobenzylidene)cyclohexanone has melting point of 104.0~104.7, $^1$H-NMR (400 MHz, CDCl$_3$): δ: 7.88 (s, 1H, =CH), 7.74 (s, 1H, =CH), 7.44 (m, 1H, ArH), 7.33 (m, 1H, ArH), 7.28 (m, 2H, ArH), 6.61 (d, 2H, J=2.0 Hz, ArH), 6.47 (t, 1H, J=2.1 Hz, ArH), 3.82 (s, 6H, OCH$_3$), 2.94 (t, 2H, J=5.6 Hz, CH$_2$), 2.76 (t, 2H, J=5.5

Hz, CH$_2$), 1.77 (quint, 2H, J=6.2 Hz, CH$_2$). $^{13}$C-NMR (400 MHz, CDCl$_3$): δ: 190.280, 160.837, 138.169, 137.948, 137.752, 136.739, 135.260, 134.694, 133.913, 130.818, 130.009, 129.827, 126.555, 108.627, 101.090, 55.706, 28.983, 28.483, 23.363. HR-MS: Calcd. For C$_{22}$H$_{21}$ClO$_3$ [M+H]$^+$: 369.1252, Found: 369.1251.

EXAMPLE 4

E-2-(3,5-dioxophenylmethylene)-cyclohexanone and 2-fluorobenzaldehyde were as the starting materials, see Example 1 for preparation method. Compound (2E,6E)-2-(3,5-dimethoxybenzylidene)-6-(2-fluorobenzylidene)cyclohexanone has melting point of 83.0~83.6, $^1$H-NMR (400 MHz, CDCl$_3$): δ: 7.82 (s, 1H, =CH), 7.72 (s, 1H, =CH), 7.30~7.39 (m, 2H, ArH), 7.16 (t, 1H, J=7.5 Hz, ArH), 7.11 (t, 1H, J=9.3 Hz, ArH), 6.60 (d, 2H, J=2.1 Hz, ArH), 6.47 (t, 1H, J=2.0 Hz, ArH), 3.82 (s, 6H, OCH$_3$), 2.94 (t, 2H, J=5.4 Hz, CH$_2$), 2.80 (t, 2H, J=5.8 Hz, CH$_2$), 1.78 (quint, 2H, J=6.5 Hz, CH$_2$). $^{13}$C-NMR (400 MHz, CDCl$_3$): δ: 190.173, 160.836, 138.570, 137.967, 137.597, 136.772, 131.009, 130.670, 130.589, 129.727, 124.009, 116.154, 115.937, 108.617, 101.088, 55.715, 28.953, 28.749, 23.246. HR-MS: Calcd. For C$_{22}$H$_{21}$FO$_3$ [M+H]$^+$: 353.1547, Found: 353.1549.

EXAMPLE 5

E-2-(3,5-dioxobenzylidene)-cyclohexanone and 2-bromobenzaldehyde were as the starting materials, see Example 1 for preparation method. Compound (2E,6E)-2-(3,5-dimethoxybenzyl-idene)-6-(2-bromobenzylidene)cyclohexanone has melting point of 111.7~112.5. $^1$H-NMR (400 MHz, CDCl$_3$): δ: 7.82 (s, 1H, =CH), 7.74 (s, 1H, =CH), 7.63 (d, 1H, J=7.9 Hz, ArH), 7.30 (m, 2H, ArH), 7.20 (t, 1H, J=8.0 Hz, ArH), 6.60 (d, 2H, J=1.9 Hz, ArH), 6.47 (t, 1H, J=1.9 Hz, ArH), 3.82 (s, 6H, —OCH$_3$), 2.93 (t, 2H, J=5.6 Hz, —CH$_2$), 2.74 (t, 2H, J=5.3 Hz, —CH$_2$), 1.77 (quint, 2H, J=6.5 Hz, —CH$_2$). $^{13}$C-NMR (400 MHz, CDCl$_3$): δ: 190.273, 160.844, 137.958, 137.894, 137.796, 136.730, 136.559, 136.196, 133.208, 130.848, 129.961, 127.178, 125.408, 108.638, 101.102, 55.720, 28.996, 28.381, 23.362. HR-MS: Calcd. For C$_{22}$H$_{21}$BrO$_3$ [M+H]$^+$: 413.0747, Found: 413.0765.

EXAMPLE 6

E-2-(3,5-dioxobenzylidene)-cyclohexanone and 3-bromobenzaldehyde were as the starting materials, see Example 1 for preparation method. Compound (2E,6E)-2-(3,5-dimethoxybenzylidene)-6-(3-bromobenzylidene)cyclohexanone has melting point of 111.9~112.7, $^1$H-NMR (400 MHz, CDCl$_3$): δ: 7.72 (s, 1H, =CH), 7.69 (s, 1H, =CH), 7.59 (s, 1H, ArH), 7.46 (d, 1H, J=7.7 Hz, ArH), 7.36 (d, 1H, J=7.6 Hz, ArH), 7.28 (t, 1H, J=7.9 Hz, ArH), 6.60 (s, 2H, ArH), 6.47 (s, 1H, ArH), 3.82 (s, 6H, OCH$_3$), 2.91 (m, 4H, CH$_2$), 1.79 (quint, 2H, J=6.3 Hz, CH$_2$). $^{13}$C-NMR (400 MHz, CDCl$_3$): δ: 190.151, 160.825, 138.269, 137.846, 137.558, 136.593, 135.402, 133.047, 131.667, 130.167, 129.157, 122.721, 108.617, 101.105, 55.676, 28.728, 28.622, 23.097. HR-MS: Calcd. For C$_{22}$H$_{21}$BrO$_3$ [M+H]$^+$: 413.0747, Found: 413.0747.

EXAMPLE 7

E-2-(3,5-dioxophenylmethylene)-cyclohexanone and 4-bromobenzaldehyde were as starting materials, see Example 1 for preparation method. Compound (2E,6E)-2-(3,5-dimethoxybenzyl-idene)-6-(4-bromophenyl-methylene)cyclohexanone has melting point of 126.4~128.6, $^1$H-NMR (400 MHz, CDCl$_3$): δ: 7.71 (s, 1H, =CH), 7.70 (s, 1H, =CH), 7.53 (d, 2H, J=8.3 Hz, ArH), 7.32 (d, 2H, J=8.3 Hz, ArH), 6.60 (d, 2H, J=1.8 Hz, ArH), 6.47 (s, 1H, ArH), 3.82 (s, 6H, OCH$_3$), 2.93 (t, 2H, J=5.4 Hz, CH$_2$), 2.88 (t, 2H, J=5.4 Hz, CH$_2$), 1.79 (quint, 2H, J=6.4 Hz, CH$_2$). $^{13}$C-NMR (400 MHz, CDCl$_3$): δ: 190.323, 160.845, 137.912, 137.454, 136.967, 136.685, 135.922, 135.069, 132.115, 131.905, 123.159, 108.617, 101.084, 55.718, 28.755, 23.137. HR-MS: Calcd. For C$_{22}$H$_{21}$BrO$_3$ [M+H]$^+$: 413.0747, Found: 413.0761.

EXAMPLE 8

E-2-(3,5-dioxobenzylidene)-cyclohexanone and 4-fluorobenzaldehyde were as starting materials, see Example 1 for preparation method. Compound (2E,6E)-2-(3,5-dimethoxybenzyl-idene)-6-(4-fluorobenzylidene)cyclohexanone has melting point of 107.2~108.3, $^1$H-NMR (400 MHz, CDCl$_3$): δ(ppm): 7.73 (s, 1H, =CH), 7.70 (s, 1H, =CH), 7.44 (d, 2H, J=8.6 Hz, ArH), 7.08 (d, 2H, J=8.5 Hz, ArH), 6.59 (d, 2H, J=1.7 Hz, ArH), 6.45 (s, 1H, ArH), 3.80 (s, 6H, OCH$_3$), 2.86~2.93 (m, 4H, CH$_2$), 1.78 (quint, 2H, J=6.1 Hz, CH$_2$). $^{13}$C-NMR (400 MHz, CDCl$_3$): δ(ppm): 190.421, 160.876, 137.996, 137.260, 136.801, 136.156, 132.622, 132.540, 132.375, 115.923, 115.709, 108.616, 101.072, 55.708, 28.765, 28.702, 23.196. HR-MS: Calcd. For C$_{22}$H$_{21}$FO$_3$ [M+H]$^+$: 353.1547, Found: 353.1575.

EXAMPLE 9

E-2-(3,5-dioxobenzylidene)-cyclohexanone and 4-chlorobenzaldehyde were as the starting materials, see Example 1 for preparation method. Compound (2E,6E)-2-(3,5-dimethoxybenzyl-idene)-6-(4-chlorobenzylidene)cyclohexanone has melting point of 124.4~124.8, $^1$H-NMR (400 MHz, CDCl$_3$): δ(ppm): 7.72 (s, 1H, =CH), 7.71 (s, 1H, =CH), 7.38 (m, 4H, ArH), 6.60 (d, 2H, J=2.1 Hz, ArH), 6.47 (t, 1H, J=2.1 Hz, ArH), 3.82 (s, 6H, OCH$_3$), 2.93 (t, 2H, J=5.6 Hz, CH$_2$), 2.87 (t, 2H, J=5.5 Hz, CH$_2$), 1.79 (quint, 2H, J=6.5 Hz, CH$_2$). $^{13}$C-NMR (400 MHz, CDCl$_3$): δ(ppm): 190.341, 160.852, 137.923, 137.417, 136.847, 136.702, 135.900, 134.816, 134.636, 131.895, 128.949, 108.613, 101.074, 55.713, 28.752, 23.144. HR-MS: Calcd. For C$_{22}$H$_{21}$ClO$_3$ [M+H]$^+$: 369.1252, Found: 369.1269.

EXAMPLE 10

E-2-(3,5-dioxobenzylidene)-cyclohexanone and cyclohexyl carbaldehyde were as starting materials, see Example 1 for preparation method. Compound (2E,6E)-2-(3,5-dimethoxybenzyl-idene)-6-(cyclohexyl methylene)cyclohexanone has melting point of 94.0~95.1, $^1$H-NMR (400 MHz, CDCl$_3$): δ(ppm): 7.64 (s, 1H, =CH), 6.73 (d, 1H, J=9.8 Hz, ArH), 6.60 (d, 2H, J=1.9 Hz, ArH), 6.45 (s, 1H, ArH), 3.81 (s, 6H, OCH$_3$), 2.86 (t, 2H, J=5.6 Hz, CH$_2$), 2.60 (t, 2H, J=5.5 Hz, CH$_2$), 2.29 (m, 1H, CH), 1.74~1.77 (m, 4H, CH$_2$), 1.67 (m, 2H, CH$_2$), 1.14~1.35 (m, 6H, CH$_2$). $^{13}$C-NMR (400 MHz, CDCl$_3$): δ(ppm): 190.633, 160.785, 146.497, 138.165, 137.117, 136.557, 134.262, 108.505, 100.872, 55.694, 37.558, 32.046, 28.853, 26.466, 26.180, 25.941, 23.040. HR-MS: Calcd. For C$_{22}$H$_{28}$O$_3$ [M+H]$^+$: 341.2111, Found: 341.2111.

EXAMPLE 11

E-2-(3,5-dioxobenzylidene)-cyclohexanone and 3-methoxybenzaldehyde were as the starting materials, see Example 1 for preparation method. Compound (2E,6E)-2-(3,5-dimethoxybenzyl-idene)-6-(3-methoxybenzylidene)cyclohexanone has melting point of 92.0~92.6, $^1$H-NMR (400 MHz, CDCl$_3$): δ(ppm): 7.76 (s, 1H, =CH), 7.71 (s, 1H, =CH), 7.32 (t, 1H, J=7.9 Hz, ArH), 7.06 (d, 1H, J=7.7 Hz, ArH), 7.00 (s, 1H, ArH), 6.90 (d, 1H, J=8.2 Hz, ArH), 6.60 (d, 2H, J=1.6 Hz, ArH), 6.50 (s, 1H, ArH), 3.84 (s, 3H, CH$_3$), 3.82 (s, 6H, OCH$_3$), 2.90 (t, 4H, J=5.2 Hz, CH$_2$), 1.80 (quint, 2H, J=6.4 Hz, CH$_2$). $^{13}$C-NMR: δ(ppm): 190.429, 160.792, 159.652, 137.955, 137.471, 137.107, 136.832, 136.619, 129.600, 123.085, 116.005, 114.455, 108.548, 100.994, 55.630, 55.507, 28.755, 28.728, 23.156. HR-MS: Calcd. For C$_{23}$H$_{24}$O$_4$[M+H]$^+$: 365.1747, Found: 365.1747.

EXAMPLE 12

300 mg (1.22 mmol) of E-2-(3,5-dioxobenzylidene)-cyclohexanone and 168 mg (1.22 mmol) of 3,4-hydroxybenzaldehyde were added to 10 mL of ethanol, 203 μL (2.43 mmol) of concentrated hydrochloric acid was added, stirred at room temperature for 30 min, 50 mL of water and 20 mL×3 ethyl acetate were added for extraction, after dried over anhydrous sodium sulfate, the solvent was evaporated, 320 mg (2E,6E)-2-(3,5-dimethoxybenzylidene)-6-(3,4-dihydroxybenzylidene)cyclohexanone as pale yellow needles was obtained by column chromatography with petroleum ether and ethyl acetate in volume ratio of 15:1, yield: 78.7%, mp 157.6~158.7. $^1$H-NMR: δ: 7.79 (s, 1H, =CH), 7.71 (s, 1H, =CH), 7.19 (s, 1H, ArH), 7.04 (d, 1H, J=8.3 Hz, ArH), 6.93 (d, 1H, J=8.2 Hz, ArH), 6.60 (s, 2H, ArH), 6.47 (d, 1H, J=1.6 Hz, ArH), 3.82 (d, 6H, J=1.6 Hz, OCH$_3$), 2.90 (m, 4H, CH$_2$), 1.79 (quint, 2H, J=5.7 Hz, CH$_2$); $^{13}$C-NMR: δ=189.808, 160.872, 147.521, 145.617, 137.848, 137.753, 137.630, 135.768, 133.608, 127.474, 124.263, 118.335, 116.360, 108.601, 101.240, 55.840, 28.557, 28.367, 22.934. HR-MS: Calcd. For C$_{22}$H$_{22}$O$_5$ [M+H]$^+$: 367.1540, Found: 367.1541.

EXAMPLE 13

E-2-(3,5-dioxobenzylidene)-cyclohexanone and 2-methoxybenzaldehyde were as the starting materials, see Example 1 for preparation method. Compound (2E,6E)-2-(3,5-dimethoxybenzyl-idene)-6-(2-methoxybenzylidene)cyclohexanone has melting point of 90.8~91.2, $^1$H-NMR (400 MHz, CDCl$_3$): δ(ppm): 7.99 (s, 1H, =CH), 7.71 (s, 1H, =CH), 7.33 (m, 2H, ArH), 6.97 (t, 1H, J=7.4 Hz, ArH), 6.92 (d, 1H, J=8.2 Hz, ArH), 6.60 (d, 2H, J=2.0 Hz, ArH), 6.46 (t, 1H, J=2.0 Hz, ArH), 3.87 (s, 3H, OCH$_3$), 3.82 (s, 6H, OCH$_3$), 2.92 (t, 2H, J=5.7 Hz, CH$_2$), 2.84 (t, 2H, J=5.5 Hz, CH$_2$), 1.77 (quint, 2H, J=6.2 Hz, CH$_2$). $^{13}$C-NMR δ(ppm): 190.502, 160.769, 158.596, 138.117, 137.105, 136.911, 136.417, 132.909, 130.533, 130.388, 125.110, 120.152, 110.817, 108.510, 100.880, 55.686, 55.611, 28.956, 28.735, 23.421. HR-MS: Calcd. For C$_{23}$H$_{24}$O$_4$[M+H]$^+$: 365.1747, Found: 365.1750.

EXAMPLE 14

E-2-(3,5-dioxobenzylidene)-cyclohexanone and 4-hydroxybenzaldehyde were as the starting materials, see Example 12 for preparation method. Compound (2E,6E)-2-(3,5-dimethoxybenzylidene)-6-(4-hydroxybenzylidene)cyclohexanone has melting point of 155.0~155.6, $^1$H-NMR (400 MHz, CDCl$_3$): δ(ppm): 7.76 (s, 1H, =CH), 7.72 (s, 1H, =CH), 7.39 (d, 2H, J=8.3 Hz, ArH), 6.90 (d, 2H, J=8.4 Hz, ArH), 6.59 (s, 2H, ArH), 6.46 (s, 1H, ArH), 6.27 (s, 1H, OH), 3.81 (s, 6H, OCH$_3$), 2.90 (m, 4H, CH$_2$), 1.79 (m, 2H, CH$_2$). $^{13}$C-NMR: δ(ppm): 191.373, 160.838, 157.381, 138.314, 138.045, 137.259, 137.102, 134.065, 133.039, 128.507, 115.982, 108.648, 101.149, 55.748, 28.860, 28.718, 23.219. HR-MS: Calcd. For C$_{22}$H$_{22}$O$_4$ [M+H]$^+$: 351.1591, Found: 351.1590.

EXAMPLE 15

E-2-(3,5-dioxybenzylidene)-cyclohexanone and 4-dimethylaminobenzaldehyde were as raw materials, see Example 1 for preparation method. Compound (2E,6E)-2-(3,5-dimethoxybenzyl-idene)-6-(4-dimethylaminobenzylidene)cyclohexanone has melting point of 109.6~110.3, $^1$H-NMR (400 MHz, CDCl$_3$): δ(ppm): 7.78 (s, 1H, =CH), 7.70 (s, 1H, =CH), 7.46 (d, 2H, J=8.8 Hz, ArH), 6.72 (d, 2H, J=8.8 Hz, ArH), 6.60 (d, 2H, J=2.0 Hz, ArH), 6.44 (s, 1H, ArH), 3.81 (s, 6H, OCH$_3$), 3.03 (s, 6H, NCH$_3$), 2.95 (t, 2H, J=6.3 Hz, CH$_2$), 2.90 (t, 2H, J=5.6 Hz), 1.80 (quint, 2H, J=6.2 Hz, CH$_2$). $^{13}$C-NMR: δ(ppm): 190.267, 160.794, 150.851, 138.751, 138.411, 137.439, 135.885, 133.004, 131.900, 124.155, 111.895, 108.468, 100.776, 55.675, 40.389, 29.099, 28.733, 23.333. HR-MS: Calcd. For C$_{24}$H$_{27}$NO$_3$[M+H]$^+$: 378.2064, Found: 378.2060.

EXAMPLE 16

E-2-(3,5-dioxybenzylidene)-cyclohexanone and 3-hydroxy-4-methoxybenzaldehyde were as raw materials, see Example 12 for preparation method. Compound (2E,6E)-2-(3,5-dimethoxy-benzylidene)-6-(3-hydroxy-4-methoxybenzylidene)cyclohexanone has melting point of 131.2-131.6, $^1$H-NMR (400 MHz, CDCl$_3$): 7.72 (s, 1H, =CH), 7.69 (s, 1H, =CH), 7.01 (d, 1H, J=8.2 Hz, ArH), 6.97 (s, 1H, ArH), 6.93 (d, 1H, J=8.2 Hz, ArH), 6.58 (d, 2H, J=1.5 Hz, ArH), 6.43 (s, 1H, ArH), 5.86 (s, 1H, OH), 3.90 (s, 3H, OCH$_3$), 3.79 (s, 6H, OCH$_3$), 2.87 (m, 4H, CH$_2$), 1.77 (quint, 2H, J=6.2 Hz, CH$_2$). $^{13}$C-NMR: δ(ppm): 190.406, 160.764, 146.897, 146.642, 138.046, 137.833, 136.960, 136.735, 134.218, 128.600, 124.835, 114.805, 113.616, 108.524, 100.915, 56.175, 55.635, 28.827, 28.664, 23.182. HR-MS: Calcd. For C$_{23}$H$_{24}$O$_5$[M+H]$^+$: 381.1697, Found: 381.1692.

EXAMPLE 17

E-2-(3,5-dioxophenylmethylene)-cyclohexanone and 4-methoxybenzaldehyde were as the starting materials, see Example 1 for preparation method. Compound (2E,6E)-2-(3,5-dimeth-oxybenzylidene)-6-(4-methoxybenzylidene)cyclohexanone has melting point of 97.7~98.1, $^1$H-NMR (400 MHz, CDCl$_3$): δ(ppm): 7.77 (s, 1H, =CH), 7.71 (s, 1H, =CH), 7.46 (d, 2H, J=8.7 Hz, ArH), 6.94 (d, 2H, J=8.7 Hz, ArH), 6.60 (d, 2H, J=1.9 Hz, ArH), 6.46 (s, 1H, ArH), 3.85 (s, 3H, CH$_3$), 3.82 (s, 6H, OCH$_3$), 2.92 (t, 4H, J=5.9 Hz, CH$_2$), 1.80 (quint, 2H, J=6.4 Hz, CH$_2$). $^{13}$C-NMR: δ(ppm): 190.280, 160.745, 160.225, 138.045, 137.273, 136.970, 136.560, 134.257, 132.562, 128.771, 114.127, 108.460, 100.849, 55.573, 28.774, 28.657, 23.150. HR-MS: Calcd. For C$_{23}$H$_{24}$O$_4$[M+H]$^+$: 365.1747, Found: 365.1747.

EXAMPLE 18

E-2-(3,5-dioxobenzylidene)-cyclohexanone and 3,5-dimethoxybenzaldehyde were as starting materials, see Example 1 for preparation method. Compound (2E,6E)-2,6-bis (3,5-dimethoxybenzylidene)cyclohexanone has melting point of 135.7~136.5, $^1$H-NMR (400 MHz, CDCl$_3$): δ(ppm): 7.71 (s, 2H, =CH), 6.60 (d, 4H, J=2.1 Hz, ArH), 6.46 (t, 2H, J=2.1 Hz, ArH), 3.82 (s, 12H, OCH$_3$), 2.92 (t, 4H, J=5.5 Hz, CH$_2$), 1.78 (quint, 2H, J=6.6 Hz, CH$_2$). $^{13}$C-NMR δ(ppm): 190.525, 160.833, 137.995, 137.243, 136.866, 108.592, 101.041, 55.702, 28.813, 23.181. HR-MS: Calcd. For C$_{24}$H$_{26}$O$_5$[M+H]$^+$: 395.1853, Found: 395.1869.

EXAMPLE 19

E-2-(3,5-dioxobenzylidene)-cyclohexanone and 4-methylsulphonylbenzaldehyde as starting materials, see Example 1 for preparation method. Compound (2E,6E)-2-(3,5-dimethoxybenzyl-idene)-6-(4-methylsulphonylbenzylidene) cyclohexanone has melting point of 162.0~163.5, $^1$H-NMR (400 MHz, CDCl$_3$): δ(ppm): 7.79 (d, 2H, J=8.2 Hz, ArH), 7.76 (s, 1H, =CH), 7.73 (s, 1H, =CH), 7.61 (d, 2H, J=8.2 Hz, ArH), 6.61 (s, 2H, ArH), 6.48 (s, 1H, ArH), 3.82 (s, 6H, OCH$_3$), 3.09 (s, 3H, SO$_2$CH$_3$), 2.95 (t, 2H, J=5.1 Hz, CH$_2$), 2.89 (t, 2H, J=5.3 Hz, CH$_2$), 1.80 (quint, 2H, J=5.6 Hz, CH$_2$). $^{13}$C-NMR: δ(ppm): 189.744, 160.713, 141.522, 139.929, 139.108, 137.843, 137.523, 136.255, 134.311, 130.899, 127.501, 108.540, 101.071, 55.543, 44.536, 28.541, 28.499, 22.860. HR-MS: Calcd. For C$_{23}$H$_{24}$O$_5$S[M+H]$^+$: 413.1417, Found: 413.1396.

EXAMPLE 20

E-2-(3,5-dioxybenzylidene)-cyclohexanone and 3,5-di-t-butyl-4-hydroxybenzaldehyde were as the starting materials, see Example 12 for preparation method. Compound (2E,6E)-2-(3,5-dimethoxybenzylidene)-6-(3,5-di-t-butyl-4-hydroxybenzylidene)cyclohexanone has m.p. of 148.2~149.9, $^1$H-NMR (400 MHz, CDCl$_3$): δ(ppm): 7.79 (s, 1H, =CH), 7.70 (s, 1H, =CH), 7.37 (s, 2H, ArH), 6.60 (s, 2H, ArH), 6.45 (s, 1H, ArH), 5.48 (s, 1H, OH), 3.82 (s, 6H, OCH$_3$), 2.903 (m, 4H, CH$_2$), 1.80 (quint, 2H, J=5.8 Hz, CH$_2$), 1.46 (s, 18H, CH$_3$). $^{13}$C-NMR δ(ppm): 190.493, 160.829, 155.078, 139.015, 138.272, 137.232, 136.481, 136.151, 133.471, 128.514, 127.638, 108.539, 100.878, 55.704, 34.704, 30.539, 28.925, 28.785, 23.435. HR-MS: Calcd. For C$_{30}$H$_{38}$O$_4$[M+H]$^+$: 463.2843, Found: 463.2829.

EXAMPLE 21

Cyclopentanone and morphine were as raw materials, preparation method same as the step (1) of Example 1 was used to give E-2-(3,5-dioxybenzylidene)-cyclopentanone with yield of 62.0% and m.p. of 98~99. $^1$H-NMR (400 MHz, CDCl$_3$): δ: 7.31 (t, 1H, J=5.2 Hz, =CH), 6.68 (d, 2H, J=2.0 Hz, ArH), 6.49 (t, 1H, J=2.0 Hz, ArH), 3.82 (s, 6H, OCH$_3$), 2.98 (td, 2H, J=2.5, 7.2 Hz, CH$_2$), 2.41 (t, 2H, J=7.9 Hz, CH$_2$), 2.03 (quint, 2H, J=7.6 Hz, CH$_2$).

E-2-(3,5-dioxybenzylidene)-cyclopentanone and benzaldehyde were as the starting materials, preparation method same as the step (2) of Example 1 was used to give (2E,5E)-2-(3,5-dimethoxybenzylidene)-5-benzylidenecyclopentanone with m.p. of 135.1~136.3. $^1$H-NMR (400 MHz, CDCl$_3$): δ: 7.59~7.60 (m, 3H, =CH, ArH), 7.52 (s, 1H, =CH), 7.45 (t, 2H, J=7.2 Hz, ArH), 7.37~7.40 (t, 1H, J=7.12 Hz, ArH), 6.75 (s, 2H, ArH), 6.51 (s, 1H, ArH), 3.83 (s, 6H, OCH$_3$), 3.11 (s, 4H, CH$_2$). $^{13}$C-NMR (400 MHz, CDCl$_3$): δ(ppm): 196.375, 160.962, 137.885, 137.707, 137.423, 135.940, 134.021, 133.964, 130.955, 129.595, 128.954, 108.879, 101.799, 55.557, 26.690, 26.658. HR-MS: Calcd. For C$_{21}$H$_{20}$O$_3$[M+H]$^+$: 321.1485, Found: 321.1475.

EXAMPLE 22

E-2-(3,5-dioxybenzylidene)-cyclopentanone and 3-chlorobenzaldehyde were as the starting materials, preparation method same as the Example 1 was used to give (2E,5E)-2-(3,5-dimethoxybenzylidene)-5-(3-chlorobenzylidene)cyclopentanone with m.p. of 145.8~147.6. $^1$H-NMR (400 MHz, CDCl$_3$): δ(ppm): 7.90 (s, 1H, =CH), 7.56~7.58 (m, 1H, ArH), 7.53 (s, 1H, =CH), 7.45~7.47 (m, 1H, ArH), 7.29~7.32 (m, 2H, ArH), 6.74 (d, 1H, ArH), 6.73 (d, 1H, ArH), 6.51 (s, 1H, ArH), 3.83 (s, 6H, OCH$_3$), 3.00~3.10 (m, 4H, CH$_2$). $^{13}$C-NMR (400 MHz, CDCl$_3$): δ(ppm): 196.050, 161.048, 139.710, 137.664, 136.288, 134.494, 134.061, 130.403, 130.333, 130.290, 129.769, 126.898, 108.956, 101.960, 55.654, 26.900, 26.564. HR-MS: Calcd. For C$_{21}$H$_{19}$ClO$_3$[M+H]$^+$: 355.1095, Found: 355.1089.

EXAMPLE 23

E-2-(3,5-dioxybenzylidene)-cyclopentanone and 2-chlorobenzaldehyde were as the starting materials, preparation method same as the Example 1 was used to give (2E,5E)-2-(3,5-dimethoxybenzylidene)-5-(2-chlorobenzylidene)cyclopentanone with m.p. of 162.4~162.9. $^1$H-NMR (400 MHz, CDCl$_3$): δ(ppm): 7.91 (s, 1H, =CH), 7.57 (d, 1H, J=6.7 Hz, ArH), 7.53 (s, 1H, =CH), 7.46 (d, 1H, J=7.6 Hz, ArH), 7.30~7.32 (m, 2H, ArH), 6.74 (s, 2H, ArH), 6.51 (s, 1H, ArH), 3.83 (s, 6H, OCH$_3$), 3.01~3.11 (m, 4H, CH$_2$). $^{13}$C-NMR (400 MHz, CDCl$_3$): δ(ppm): 196.121, 161.080, 139.751, 137.709, 136.326, 134.542, 134.119, 130.431, 130.377, 130.320, 129.863, 126.914, 108.987, 101.982, 55.705, 26.956, 26.613. HR-MS: Calcd. For C$_{21}$H$_{19}$ClO$_3$[M+H]$^+$: 355.1095, Found: 355.1086.

EXAMPLE 24

E-2-(3,5-dioxybenzylidene)-cyclopentanone and 2-fluorobenzaldehyde were as the starting materials, preparation method same as the Example 1 was used to give (2E,5E)-2-(3,5-dimethoxybenzylidene)-5-(2-fluorobenzylidene)cyclopentanone with m.p. of 133.6~134.9. $^1$H-NMR (400 MHz, CDCl$_3$): δ(ppm): 7.81 (s, 1H, =CH), 7.59 (d, 1H, J=6.7 Hz, ArH), 7.53 (s, 1H, =CH), 7.46 (d, 1H, J=8.3 Hz, ArH), 7.21 (t, 1H, J=7.6 Hz, ArH), 7.14 (t, 1H, J=8.9 Hz, ArH), 6.75 (s, 2H, ArH), 6.51 (s, 1H, ArH), 3.84 (s, 6H, OCH$_3$), 3.03~3.13 (m, 4H, CH$_2$). $^{13}$C-NMR (400 MHz, CDCl$_3$): δ(ppm): 196.092, 161.058, 139.295, 137.732, 134.418, 131.338, 131.253, 130.338, 125.553, 125.497, 124.386, 116.273, 116.054, 108.975, 101.954, 55.672, 26.801, 26.723. HR-MS: Calcd. For C$_{21}$H$_{19}$FO$_3$[M+H]$^+$: 339.1391, Found: 339.1386.

EXAMPLE 25

E-2-(3,5-dioxybenzylidene)-cyclopentanone and 2-bromobenzaldehyde were as the starting materials, preparation method same as the Example 1 was used to give (2E,5E)-2-(3,5-dimethoxybenzylidene)-5-(2-bromobenzylidene)cyclopentanone with m.p. of 159.0~160.3. $^1$H-NMR (400 MHz, CDCl$_3$): δ(ppm): 7.81 (s, 1H, =CH), 7.59 (t, 1H, J=7.7 Hz, ArH), 7.53 (s, 1H, =CH), 7.34~7.39 (m, 1H, ArH), 7.21 (t, 1H, J=7.6 Hz, ArH), 7.14 (t, 1H, J=9.6 Hz, ArH), 6.75 (s, 2H, ArH), 6.51 (s, 1H, ArH), 3.84 (s, 6H, OCH$_3$), 3.04~3.13 (m, 4H, CH$_2$). $^{13}$C-NMR (400 MHz, CDCl$_3$): δ(ppm): 196.063, 161.071, 139.772, 137.720, 137.691, 135.811, 134.545, 133.653, 132.434, 130.562, 130.394, 127.520, 126.720, 108.976, 101.979, 55.703, 26.957, 26.473. HR-MS: Calcd. For C$_{21}$H$_{19}$BrO$_3$[M+H]$^+$: 399.0590, Found: 399.0584.

EXAMPLE 26

E-2-(3,5-dioxybenzylidene)-cyclopentanone and 3-bromobenzaldehyde were as the starting materials, preparation method same as the Example 1 was used to give (2E,5E)-2-(3,5-dimethoxybenzylidene)-5-(3-bromobenzylidene)cyclopentanone with m.p. of 141.8~142.7. $^1$H-NMR (400 MHz, CDCl$_3$): δ(ppm): 7.73 (s, 1H, =CH), 7.50~7.53 (m, 4H, ArH, =CH), 7.32 (t, 1H, J=7.7 Hz, ArH), 6.75 (s, 2H, ArH), 6.52 (s, 1H, ArH), 3.84 (s, 6H, OCH$_3$), 3.11~3.13 (m, 4H, CH$_2$). $^{13}$C-NMR (400 MHz, CDCl$_3$): δ(ppm): 196.237, 161.097, 138.830, 138.117, 137.668, 137.584, 134.639, 133.345, 132.418, 132.305, 130.519, 129.558, 123.137, 109.041, 102.069, 55.700, 26.755, 26.693. HR-MS: Calcd. For C$_{21}$H$_{19}$BrO$_3$[M+H]$^+$: 399.0590, Found: 399.0573.

EXAMPLE 27

E-2-(3,5-dioxybenzylidene)-cyclopentanone and 4-bromobenzaldehyde were as the starting materials, preparation method same as the Example 1 was used to give (2E,5E)-2-(3,5-dimethoxybenzylidene)-5-(4-bromobenzylidene)cyclopentanone with m.p. of 182.0~183.3. $^1$H-NMR (400 MHz, CDCl$_3$): δ(ppm): 7.57 (d, 2H, J=8.4 Hz, ArH), 7.52 (s, 2H, =CH), 7.45 (d, 2H, J=8.4 Hz, ArH), 6.74 (s, 2H, ArH), 6.51 (s, 1H, ArH), 3.84 (s, 6H, OCH$_3$), 3.04~3.14 (m, 4H, CH$_2$). $^{13}$C-NMR (400 MHz, CDCl$_3$): δ(ppm): 196.373, 161.116, 138.169, 137.733, 134.952, 134.503, 132.803, 132.335, 132.318, 124.064, 109.053, 102.019, 55.736, 26.775. HR-MS: Calcd. For C$_{21}$H$_{19}$BrO$_3$[M+H]$^+$: 399.0590, Found: 399.0588.

EXAMPLE 28

E-2-(3,5-dioxybenzylidene)-cyclopentanone and 4-fluorobenzaldehyde were as the starting materials, preparation method same as the Example 1 was used to give (2E,5E)-2-(3,5-dimethoxybenzylidene)-5-(4-fluorobenzylidene)cyclopentanone with m.p. of 147.7~149.4. $^1$H-NMR (400 MHz, CDCl$_3$): δ(ppm): 7.54~7.59 (m, 3H, ArH, =CH), 7.50 (s, 1H, =CH), 7.11 (t, 2H, J=8.5 Hz, ArH), 6.73 (s, 1H, ArH), 6.72 (s, 1H, ArH), 6.49 (s, 1H, ArH), 3.82 (s, 6H, OCH$_3$), 3.04~3.13 (m, 4H, CH$_2$). $^{13}$C-NMR (400 MHz, CDCl$_3$): δ(ppm): 196.527, 161.144, 137.899, 137.826, 137.095, 134.343, 133.063, 133.004, 132.921, 116.395, 116.178, 109.054, 108.786, 101.988, 55.756, 26.821, 26.696. HR-MS: Calcd. For C$_{21}$H$_{19}$FO$_3$[M+H]$^+$: 339.1391, Found: 339.1377.

EXAMPLE 29

E-2-(3,5-dioxybenzylidene)-cyclopentanone and 4-chlorobenzaldehyde were as the starting materials, preparation method same as the Example 1 was used to give (2E,5E)-2-(3,5-dimethoxybenzylidene)-5-(4-chlorobenzylidene)cyclopentanone with m.p. of 178.5~179.2. $^1$H-NMR (400 MHz, CDCl$_3$): δ(ppm): 7.52 (m, 4H, ArH, =CH), 7.41 (d, 2H, J=8.4 Hz, ArH), 6.75 (s, 1H, ArH), 6.74 (s, 1H, ArH), 6.51 (s, 1H, ArH), 3.84 (s, 6H, OCH$_3$), 3.05~3.14 (m, 4H, CH$_2$). $^{13}$C-NMR (400 MHz, CDCl$_3$): δ(ppm): 196.362, 161.115, 137.996, 137.749, 135.650, 134.542, 134.454, 132.750, 132.135, 129.352, 109.048, 102.006, 55.734, 26.790, 26.753. HR-MS: Calcd. For C$_{21}$H$_{19}$ClO$_3$[M+H]$^+$: 355.1095, Found: 355.1081.

EXAMPLE 30

E-2-(3,5-dioxybenzylidene)-cyclopentanone and cyclohexylbenzaldehyde were as the starting materials, preparation method same as the Example 1 was used to give (2E,5E)-2-(3,5-dimethoxybenzylidene)-5-(cyclohexylbenzylidene)cyclopentanone with m.p. of 110.5~111.7. $^1$H-NMR (400 MHz, CDCl$_3$): δ(ppm): 7.42 (s, 1H, =CH), 6.71 (s, 2H, ArH), 6.61 (d, 1H, J=9.8 Hz, =CH), 6.49 (s, 1H, ArH), 3.82 (s, 6H, OCH$_3$), 3.00 (td, 2H, J=2.5 Hz, 7.9 Hz, CH$_2$), 2.72 (td, 2H, J=2.7 Hz, 7.7 Hz, CH$_2$), 2.19~2.32 (m, 1H, CH), 1.74~1.78 (m, 2H, CH$_2$), 1.67~1.70 (m, 2H, CH$_2$), 1.14~1.36 (m, 6H, CH$_2$). $^{13}$C-NMR (400 MHz, CDCl$_3$): δ(ppm): 196.187, 161.015, 143.279, 138.995, 137.883, 136.536, 133.450, 108.844, 101.709, 55.649, 39.179, 31.873, 26.409, 26.122, 25.812, 23.816. HR-MS: Calcd. For C$_{21}$H$_{26}$O$_3$[M+H]$^+$: 327.1955, Found: 327.1953.

EXAMPLE 31

E-2-(3,5-dioxybenzylidene)-cyclopentanone and 3-methoxybenzaldehyde were as the starting materials, preparation method same as the Example 1 was used to give (2E,5E)-2-(3,5-dimethoxybenzylidene)-5-(3-methoxybenzylidene)cyclopentanone with m.p. of 125.0~126.2. $^1$H-NMR (400 MHz, CDCl$_3$): δ(ppm): 7.56 (s, 1H, =CH), 7.52 (s, 1H, =CH), 7.36 (t, 1H, J=7.8 Hz, ArH), 7.20 (d, 1H, J=7.7 Hz, ArH), 7.12 (s, 1H, ArH), 6.94 (dd, 1H, J=1.8 Hz, 8.3 Hz, ArH), 6.75 (s, 1H, ArH), 6.75 (s, 1H, ArH), 6.51 (s, 1H, ArH), 3.85 (s, 3H, OCH$_3$), 3.83 (s, 6H, OCH$_3$), 3.11 (s, 4H, CH$_2$). $^{13}$C-NMR (400 MHz, CDCl$_3$): δ(ppm): 196.505, 161.073, 159.964, 137.969, 137.809, 137.769, 137.358, 134.151, 134.101, 129.992, 123.588, 116.266, 115.380, 108.979, 101.927, 55.690, 55.570, 26.798. HR-MS: Calcd. For C$_{22}$H$_{22}$O$_4$[M+H]$^+$: 351.1591, Found: 351.1578.

EXAMPLE 32

E-2-(3,5-dioxybenzylidene)-cyclopentanone and 3,4-dihydroxybenzaldehyde were as the starting materials, preparation method same as the Example 12 was used to give (2E,5E)-2-(3,5-dimethoxybenzylidene)-5-(3,4-dihydroxybenzylidene)cyclopentanone. HR-MS: Calcd. For C$_{21}$H$_{20}$O$_5$ M$^+$: 353.1384, Found: 352.1385.

EXAMPLE 33

E-2-(3,5-dioxybenzylidene)-cyclopentanone and 2-methoxybenzaldehyde were as the starting materials, preparation method same as the Example 1 was used to give (2E,5E)-2-(3,5-dimethoxybenzylidene)-5-(2-methoxybenzylidene)cyclopentanone with m.p. of 170.4~171.7. $^1$H-NMR (400 MHz, CDCl$_3$): δ(ppm): 8.02 (s, 1H, =CH), 7.54 (d, 1H, J=7.7 Hz, ArH), 7.51 (s, 1H, =CH), 7.36 (t, 1H, J=8.2 Hz, ArH), 7.01 (t, 1H, J=7.5 Hz, ArH), 6.94 (d, 1H, J=8.3 Hz, ArH), 6.74 (d, 2H, J=1.7 Hz, ArH), 6.50 (s, 1H, ArH), 3.89 (s, 3H, OCH$_3$), 3.83 (s, 6H, OCH$_3$), 3.01~3.10 (m, 4H, CH$_2$). $^{13}$C-NMR (400 MHz, CDCl$_3$): δ(ppm): 196.487, 161.040, 159.242, 138.334, 137.959, 137.425, 133.648, 131.189, 130.069, 128.700, 125.097, 120.556, 111.096, 108.877, 101.777, 55.796, 55.673, 26.988, 26.863. HR-MS: Calcd. For C$_{22}$H$_{22}$O$_4$[M+H]$^+$: 351.1591, Found: 351.1575.

EXAMPLE 34

E-2-(3,5-dioxybenzylidene)-cyclopentanone and 4-hydroxybenzaldehyde were as the starting materials, preparation method same as the Example 12 was used to give (2E,5E)-2-(3,5-dimethoxybenzylidene)-5-(4-hydroxybenzylidene)cyclopentanone with m.p. of 253.4~255.3. $^1$H-NMR (400 MHz, CDCl$_3$): δ(ppm): 10.10 (s, 1H, OH), 7.52 (d, 2H, J=8.3 Hz, ArH), 7.36 (s, 1H, =CH), 7.30 (s, 1H, =CH), 6.86 (d, 2H, J=8.3 Hz, ArH), 6.80 (s, 2H, ArH), 6.55 (s, 1H, ArH), 3.76 (s, 6H, OCH$_3$), 2.94~3.10 (m, 4H, CH$_2$). $^{13}$C-NMR (400 MHz, CDCl$_3$), δ(ppm): 195.023, 160.557, 159.245, 138.635, 137.340, 134.084, 133.392, 132.957, 131.854, 126.519, 115.998, 108.393, 101.552, 55.361, 55.281, 25.966. HR-MS: Calcd. For C$_{21}$H$_{20}$O$_4$[M+H]$^+$: 337.1434, Found: 337.1452.

EXAMPLE 35

E-2-(3,5-dioxybenzylidene)-cyclopentanone and 4-dimethylaminobenzaldehyde were as the starting materials, preparation method same as the Example 1 was used to give (2E,5E)-2-(3,5-dimethoxybenzylidene)-5-(4-dimethylaminobenzylidene)cyclopentanone with m.p. of 194.4~196.4. $^1$H-NMR (400 MHz, CDCl$_3$): δ(ppm): 7.58 (s, 1H, =CH), 7.53 (d, 2H, J=8.9 Hz, ArH), 7.46 (s, 1H, =CH), 6.75 (m, 4H, ArH), 6.49 (s, 1H, ArH), 3.83 (s, 6H, OCH$_3$), 3.07~3.10 (m, 4H, CH$_2$), 3.05 (s, 6H, CH$_3$). $^{13}$C-NMR (400 MHz, CDCl$_3$): δ (ppm): 196.318, 161.069, 151.343, 139.173, 138.343, 135.583, 133.223, 132.644, 132.564, 124.053, 112.171, 108.834, 101.583, 55.731, 40.402, 26.938, 26.896. HR-MS: Calcd. For C$_{23}$H$_{26}$NO$_3$[M+H]$^+$: 364.1907, Found: 364.1906.

EXAMPLE 36

E-2-(3,5-dioxybenzylidene)-cyclopentanone and 3-hydroxy-4-methoxybenzaldehyde were as the starting materials, preparation method same as the Example 12 was used to give (2E,5E)-2-(3,5-dimethoxybenzylidene)-5-(3-hydroxy-4-methoxybenzylidene)cyclopentanone with m.p. of 199.1~199.5. $^1$H-NMR (400 MHz, CDCl$_3$): δ(ppm): 7.55 (s, 1H, =CH), 7.50 (s, 1H, =CH), 7.20 (d, 1H, J=8.2 Hz, ArH), 7.10 (s, 1H, ArH), 7.00 (d, 1H, J=8.0 Hz, ArH), 6.75 (s, 2H, ArH), 6.51 (s, 1H, ArH), 5.93 (s, 1H, OH), 3.95 (s, 3H, OCH$_3$), 3.83 (s, 6H, OCH$_3$), 3.05~3.15 (m, 4H, CH$_2$). $^{13}$C-NMR (400 MHz, CDCl$_3$): δ(ppm): 195.113, 160.633, 148.856, 147.806, 138.718, 137.416, 134.336, 133.847, 131.975, 127.070, 125.128, 116.002, 114.707, 108.439, 101.674, 55.698, 55.605, 55.429, 55.342, 26.024. HR-MS: Calcd. For C$_{22}$H$_{22}$O$_5$[M+H]$^+$: 367.1540, Found: 367.1524.

EXAMPLE 37

E-2-(3,5-dioxybenzylidene)-cyclopentanone and 4-methoxybenzaldehyde were as the starting materials, preparation method same as the Example 1 was used to give (2E,5E)-2-(3,5-dimethoxybenzylidene)-5-(4-methoxybenzylidene)cyclopentanone with m.p. of 138.9~140.0. $^1$H-NMR (400 MHz, CDCl$_3$): δ(ppm): 7.55~7.58 (m, 3H, =CH, ArH), 7.49 (s, 1H, =CH), 6.97 (d, 2H, J=8.6 Hz, ArH), 6.75 (s, 1H, ArH), 6.74 (s, 1H, ArH), 6.50 (s, 1H, ArH), 3.86 (s, 3H, OCH$_3$), 3.83 (s, 6H, OCH$_3$), 3.06~3.10 (m, 4H, CH$_2$). $^{13}$C-NMR (400 MHz, CDCl$_3$): δ(ppm): 196.433, 161.030, 160.921, 138.324, 137.951, 135.142, 134.163, 133.504, 132.896, 128.834, 114.582, 108.891, 101.747, 55.663, 26.773, 26.705. HR-MS: Calcd. For C$_{22}$H$_{22}$O$_4$[M+H]$^+$: 351.1591, Found: 351.1578.

EXAMPLE 38

E-2-(3,5-dioxybenzylidene)-cyclopentanone and 3,5-dimethoxybenzaldehyde were as the starting materials, preparation method same as the Example 1 was used to give (2E,5E)-2-(3,5-dimethoxybenzylidene)-5-(3,5-dimethoxybenzylidene)cyclopentanone with m.p. of 159.6~160.4. $^1$H-NMR (400 MHz, CDCl$_3$): δ(ppm): 7.51 (s, 2H, =CH), 6.74 (s, 4H, ArH), 6.51 (s, 2H, ArH), 3.83 (s, 12H, OCH$_3$), 3.10 (s, 4H, CH$_2$). $^{13}$C-NMR (400 MHz, CDCl$_3$): δ(ppm): 196.455, 161.066, 137.925, 137.787, 134.181, 108.976, 101.947, 55.679, 26.785. HR-MS: Calcd. For C$_{23}$H$_{24}$O$_5$[M+H]$^+$: 381.1697, Found: 381.1683.

EXAMPLE 39

E-2-(3,5-dioxybenzylidene)-cyclopentanone and 4-methylsulphonylbenzaldehyde were as the starting materials, preparation method same as the Example 1 was used to give (2E,5E)-2-(3,5-dimethoxybenzylidene)-5-(4-methylsulphonylbenzylidene)cyclopentanone. $^1$H-NMR (400 MHz, CDCl$_3$): δ(ppm): 8.08 (d, 2H, J=8.3 Hz, ArH), 7.75 (d, 2H, J=8.4 Hz, ArH), 7.58 (s, 1H, =CH), 7.56 (s, 1H, =CH), 6.75 (d, 2H, J=2.0 Hz, ArH), 6.53 (t, 1H, J=2.0 Hz, ArH), 3.84 (s, 6H, OCH$_3$), 3.14~3.16 (m, 4H, CH$_2$), 3.09 (s, 3H, CH$_3$SO$_2$). $^{13}$C-NMR (400 MHz, CDCl$_3$): δ(ppm): 161.186, 141.402, 141.069, 140.606, 137.534, 137.265, 135.393, 131.394, 131.334, 128.090, 109.184, 102.235, 55.780, 44.805, 26.886, 26.791. HR-MS: Calcd. For C$_{22}$H$_{32}$O$_5$S[M+H]$^+$: 399.1261, Found: 399.1262.

EXAMPLE 40

E-2-(3,5-dioxybenzylidene)-cyclopentanone and 3,5-di-tert-butylbenzaldehyde were as the starting materials, preparation method same as the Example 12 was used to give (2E,5E)-2-(3,5-dimethoxybenzylidene)-5-(3,5-di-tert-butylbenzylidene)cyclopentanone with m.p. of 216.9~218.3. $^1$H-NMR (400 MHz, CDCl$_3$): δ(ppm): 7.59 (s, 1H, =CH), 7.49 (s, 3H, =CH, ArH), 6.75 (s, 2H, ArH), 6.50 (s, 1H, ArH), 5.58 (s, 1H, OH), 3.83 (s, 6H, OCH3), 3.11 (s, 4H, CH$_2$), 1.48 (s, 18H, CH$_3$). $^{13}$C-NMR (400 MHz, CDCl$_3$): δ(ppm): 196.462, 161.050, 155.857, 138.537, 138.063, 136.625, 135.877, 134.254, 133.317, 128.802, 127.601, 108.841, 101.840, 55.664, 34.687, 30.464, 26.910, 26.830. HR-MS: Calcd. For C$_{29}$H$_{30}$O$_4$[M+H]$^+$: 449.2686, Found: 449.2686.

The effects on tumor cell proliferation: the antiproliferative activities of α-(3,5-dimethoxy-benzylidene)-α'-hydrocarbonyl methylene cyclic ketone on human hepatoma HepG2 tumor cell lines and human cutaneous melanoma A16-F10 cell lines were evaluated using methyl thiazolyl tetrazolium (MTT) assay.

Experimental procedures are performed as follows: tumor cells in DMEM culture medium containing 10% fetal bovine serum, 100 U·mL$^{-1}$ penicillin and 100 U·mL$^{-1}$ streptomycin were cultured in an incubator under 5% CO$_2$ and saturated humidity at 37. Test compounds were dissolved in dimethyl sulfoxide and then diluted with DMEM culture medium to the corresponding concentration, wherein the final concentration of dimethyl sulfoxide was less than 0.01%.

The tumor cells in the exponential growth phase were taken out, digested with trypsin, counted, and the number of the cells was adjusted with the culture solution to 1×105 cells/mL, then the cells were inoculated into 96-well plates with each well 200 μL and cultured for 12 h, followed by added with the drug. Negative control group, the blank control group and experimental groups were separately set up, each group with three double-wells. The negative control group was only added with cells but without the drug, the blank control group wad only added with dimethyl sulfoxide solution. The experimental group was added at each well with 11 μL solution containing different concentrations of the sample to be tested, such that the final concentration of the drug were 40.0, 20.0, 10.0, 5.0, 1.0 and 0.1 g/mL. The cells were cultured for additional 48 h in a incubator with 5% CO$_2$ at 37, subsequently the culture solution was gently sucked out and each well was added with 200 μL 0.5 mg/mL of MTT solution. The cells were cultured for another 6 h, then the MTT culture solution was sucked out and each well was added with 150 μL dimethyl sulfoxide, followed by oscillation dissolved for 10 min. The absorbance OD values in each well were measured at the measurement wavelength 570 nm and the reference wavelength 630 nm using a microplate reader. The experiment was repeated three times, wherein the inhibition rate (%)=(negative control OD value−test compound OD value)/(negative control OD value−blank control OD value)× 100%. The results are shown in Table 1 and Table 2.

Determination of the inhibitory effect of the compound on EGFR: the kinase activity of EGFR was detected according to time-resolved fluorescence detection technology to evaluate automatic phosphorylation levels. The test compound was dissolved in 100% DMSO, diluted with 25 mM HEPES (pH=7.4) to the desired concentration, added into each well with 10 μL of the test compounds and 10 μL solution containing 5 ng EGFR, then cultured for 10 min at room temperature using the recombinase diluted by 100 mM HEPES with a dilution ratio of 1:80, subsequently added with 10 μL solution containing 20 mM HEPES, 2 mM $MnCl_2$, 100 μM $Na_3VO_4$, 1 mM DTT buffer, and 20 μL of 0.1 mM ATP and 50 mM $MgCl_2$ and cultured for 1 h. The positive group in each plate was added with ATP-$MgCl_2$ enzyme, the negative control group without adding with ATP-$MgCl_2$ enzyme, the liquid was sucked out completely after cultured for 1 h, and each well was washed with buffer for three times. The wells were added with 75 μL anti-phosphorylated tyrosine antibody containing 400 ng europium labeling and cultured 1 h, washed, then added with enhancing solution. At the excitation wavelength 340 nm and the emission wavelength 615 nm, the fluorescence intensities were detected by using Victor type 2 time-resolved luminoscope, wherein the inhibitory rate of the compound on automatic phosphorylation: the inhibitory rate of autophosphorylation=100%−[(negative control)/(positive control−negative control)]. The results are shown in Table 1.

TABLE 1

Compound's anti-proliferative effect on tumor cells and inhibitory effect on EGFR 1

| Compound | R | anti-proliferation $IC_{50}$ [μM] Hep G2 | A16-F10 | EGFR $IC_{50}$ [μM] |
|---|---|---|---|---|
| (2E,6E)-2-(3,5-dimethoxybenzylidene)-6-benzylidenecyclohexanone | Ph | 4.74 | 2.45 | 1.68 |
| (2E,6E)-2-(3,5-dimethoxybenzylidene)-6-(3-chlorobenzylidene)cyclohexanone | 3-ClPh | 6.11 | 5.17 | 2.27 |
| (2E,6E)-2-(3,5-dimethoxybenzylidene)-6-(2-chlorobenzylidene)cyclohexanone | 2-ClPh | 5.67 | 3.23 | 1.54 |
| (2E,6E)-2-(3,5-dimethoxybenzylidene)-6-(2-fluorobenzylidene)cyclohexanone | 2-FPh | 7.53 | 5.64 | 2.17 |
| (2E,6E)-2-(3,5-dimethoxybenzylidene)-6-(2-bromobenzylidene)cyclohexanone | 2-BrPh | 32.20 | 12.42 | 8.08 |
| (2E,6E)-2-(3,5-dimethoxybenzylidene)-6-(3-bromobenzylidene)cyclohexanone | 3-BrPh | 16.67 | 10.78 | 6.85 |
| (2E,6E)-2-(3,5-dimethoxybenzylidene)-6-(4-bromobenzylidene)cyclohexanone | 4-BrPh | 29.16 | 12.27 | 7.12 |
| (2E,6E)-2-(3,5-dimethoxybenzylidene)-6-(4-fluorobenzylidene)cyclohexanone | 4-FPh | 12.09 | 7.63 | 5.69 |
| (2E,6E)-2-(3,5-dimethoxybenzylidene)-6-(4-chlorobenzylidene)cyclohexanone | 4-ClPh | 25.48 | 18.41 | 15.32 |
| (2E,6E)-2-(3,5-dimethoxybenzylidene)-6-(cyclohexylmethylene)cyclohexanone | c-$C_6H_{11}$ | 17.17 | 12.21 | 7.52 |
| (2E,6E)-2-(3,5-dimethoxybenzylidene)-6-(3-methoxybenzylidene)cyclohexanone | 3-$CH_3$OPh | 17.24 | 9.72 | 6.13 |
| (2E,6E)-2-(3,5-dimethoxybenzylidene)-6-(3,4-dihydroxybenzylidene)cyclohexanone | 3,4-diHOPh | 1.01 | 0.71 | 0.43 |
| (2E,6E)-2-(3,5-dimethoxybenzylidene)-6-(2-methoxybenzylidene)cyclohexanone | 2-$CH_3$OPh | >200 | >200 | 20.89 |
| (2E,6E)-2-(3,5-dimethoxybenzylidene)-6-(4-hydrobenzylidene)cyclohexanone | 4-HOPh | 10.47 | 3.28 | 4.66 |
| (2E,6E)-2-(3,5-dimethoxybenzylidene)-6-(4-dimethylaminobenzylidene)cyclohexanone | 4-$(CH_3)_2$NPh | 11.76 | 5.84 | 3.98 |
| (2E,6E)-2-(3,5-dimethoxybenzylidene)-6-(3-hydroxyl-4-methoxybenzylidene)cyclohexanone | 3-HO-4-$CH_3$OPh | 11.05 | 7.04 | 5.37 |
| (2E,6E)-2-di-(3,5-dimethoxybenzylidene)cyclohexanone | 4-$CH_3$OPh | 58.07 | 32.65 | 18.67 |
| (2E,6E)-2,6-(3,5-dimethoxybenzylidene)-6-(3,5-dimethoxybenzylidene)cyclohexanone | 3,5-di $CH_3$OPh | 8.56 | 4.71 | 2.08 |
| (2E,6E)-2-(3,5-dimethoxybenzylidene)-6-(4-methylsulphonylbenzylidene)cyclohexanone | 4-$CH_3SO_2$Ph | 6.68 | 3.58 | 1.96 |
| (2E,6E)-2-(3,5-dimethoxybenzylidene)-6-(3,5-di-tert-butyl -4-hydroxybenzylidene)cyclohexanone | 3,5-$(CH_3)_3$C-4-HOPh | 11.11 | 7.69 | 4.81 |
| curcumin |  | 26.99 | 18.65 | 8.65 |
| erlotinib |  | 0.12 | 0.2 | 0.03 |

Pharmacological Test results in Table 1 show that most compounds have a strong inhibitory activity on the proliferation of human hepatoma HepG2 cell lines and cutaneous melanoma A16-F10 cell lines. Except (2E,6E)-2-(3,5-dimethoxybenzylidene)-6-(2-bromobenzylidene)-cyclohexanone, (2E,6E)-2-(3,5-methylene-dimethoxyphenyl)-6-(4-bromophenyl-methylene)-cyclohexanone, (2E,6E)-2-(3,5- dimethoxybenzylidene) 6-(2-methoxybenzylidene)cyclohexanone, (2E,6E)-2-(3,5-dimethoxybenzylidene)-6-(4-methoxybenzylidene)cyclohexanone, anti-proliferative effect of other compounds on HepG2 tumor cell lines was significantly stronger than curcumin. Except (2E,6E)-2-(3,5-dimethoxybenzylidene)-6-(2-methoxybenzylidene)Cyclohexanone, (2E,6E)-2-(3,5-dimethoxybenzylidene)-6-(4-methoxybenzylidene)cyclohexanone, the anti-proliferative effect of the rest of the compounds on cutaneous melanoma A16-F10 cell lines was significantly stronger than curcumin. Wherein (2E,6E)-2-(3,5-dimethoxybenzyl-idene )-6-(3,4-dihydroxy-benzylidene)cyclohexanone has maximum anti-tumor activity, with an IC50 value<1 μM. All of the compounds have a good inhibitory effect on the epidermal growth factor receptor (EGFR).

TABLE 2

Anti-proliferative effect of compound on HepG2 tumor cells

| Compound | R | $IC_{50}$ [μM] |
|---|---|---|
| (2E,5E)-2-(3,5-dimethoxybenzylidene)-5-benzylidenecyclopentanone | Ph | 11.29 |
| (2E,5E)-2-(3,5-dimethoxybenzylidene)-5-(2-chlorobenzylidene)cyclopentanone | 2-ClPh | 41.51 |
| (2E,5E)-2-(3,5-dimethoxybenzylidene)-5-(4-fluorobenzylidene)cyclopentanone | 4-FPh | 79.91 |
| (2E,5E)-2-(3,5-dimethoxybenzylidene)-5-(3-methoxybenzylidene)cyclopentanone | 3-$CH_3$OPh | 48.75 |
| (2E,5E)-2-(3,5-dimethoxybenzylidene)-5-(3,4-dihydroxybenzylidene)cyclopentanone | 3,4-diHOPh | 7.63 |
| curcumin | | 26.99 |
| erlotinib | | 0.12 |

Pharmacological test results of Table 2 show that the five compounds have an antiproliferative effect on HepG2 tumor cell lines, wherein the activity of (2E,5E)-2-(3,5-dimethoxybenzylidene) -5-benzylidenecyclopentanone and (2E,5E)-2-(3,5-dimethoxybenzylidene)-5-(3,4-dihydroxy-cyclopentanone)cyclopentanone was significantly stronger than curcumin.

Comparing the test results in Table 1 and Table 2, it is shown that, in the presence of the same substituent R, the antiproliferative effect of α-(3,5-dimethoxybenzylidene)-α'-hydrocarbonylmethylene cyclohexanone on HepG2 tumor cell lines is greater than that of α-(3,5-dimethoxy-benzylidene)-α'-hydrocarbonyl methylene cyclopentanone.

The invention provides an antitumor agent, including α-(3, 5-dimethoxybenzy-lidene)-α'-hydrocarbonyl methylene cyclic ketone or a medically acceptable salts and pharmaceutically acceptable carriers thereof. The said compound or medically acceptable salts thereof may be administered alone or formulated by combining with one or more acceptable carriers for administration, for example, in the form of solvents, diluents and the like, they may also be administered in oral dosage form such as tablets, capsules, dispersible powders, granules and the like. Various formulations of the pharmaceutical compositions of the present invention may be prepared according to methods well known in the pharmaceutical art. The percentage by weight of the compound in antitumor agent is ranging from 0.05 to 90%, and more preferably 15-60%, the compound can be administered in accordance with 0.005~5000 mg/kg/day, but also can be administered beyond this dose range according to the severity of the disease or different dosage forms.

The curcumin derivatives also may combined with other anticantumor agents, such as alkylating agents, antimetabolites, topoisomerase inhibitors, mitotic inhibitors, DNA insert agents, combination therapy may produce a synergistic effect and thus help improve treatment results, wherein tumors includes human cancer cell lines Hep G2 hepatoma cell lines and human cutaneous melanoma A16-F10 cell lines.

Above are only embodiments of the present invention, which are not intended to limit the scope of the present invention, any equivalent formulas or equivalent process transformation made by use of the present invention specification, or any direct or indirect use in related technical fields are similarly included within the scope of patent protection of the invention.

The invention claimed is:
1. A compound of α-(3,5-dimethoxybenzylidene)-α'-hydrocarbyl methylene cyclic ketone, which formula is:

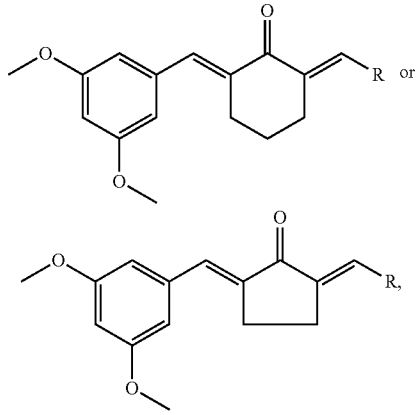

wherein R is selected from aryl or alkyl group.

2. A compound of α-(3,5-dimethoxybenzylidene)-α'-hydrocarbyl methylene cyclic ketone according to claim 1, wherein the formula of said aryl group is

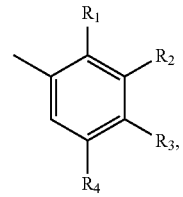

wherein $R_1$ is selected from hydrogen, hydroxy, halogen, amino, methylsulphonyl, alkoxy containing 1 to 4 carbon, alkyl, haloalkyl or alkylamino group, $R_2$ is selected from hydrogen, hydroxy, halogen, amino, methylsulphonyl, alkoxy containing 1 to 4 carbon, alkyl, haloalkyl or alkylamino group, $R_3$ is selected from hydrogen, hydroxy, halogen, amino, containing 1 to 4 carbon, alkoxy containing 1 to 4 carbon, alkyl, haloalkyl or alkylamino, $R_4$ is selected from hydrogen, hydroxy, halogen, amino, methylsulphonyl, alkoxy containing 1 to 4 carbon, alkyl, haloalkyl or alkylamino group; the alkyl group is selected from alkyl containing 1 to 8 carbon.

3. A method of preparing the compound of α-(3,5-dimethoxybenzylidene)-α'-hydrocarbyl methylene cyclic ketone, wherein it comprises the following steps: mix the cyclic ketone and morpholine and follow azeotropic dehydration to obtain enamine; the enamine and 3,5-dimethoxybenzaldehyde occur condensation reaction to obtain E-α-(3,5-dioxobenzylid-ene)-cyclic ketone; the condensation of E-α-(3,5-dioxobenzylidene)-cyclic ketone with alkyl or aryl formaldehyde under acidic or basic conditions affords α-(3, 5-dimethoxybenzylidene) -α'-hydrocarbyl methylene cyclic ketone; which formula of the compound of α-(3,5- dimethoxybenzylidene)-α'-hydrocarbyl methylene cyclic ketone is:

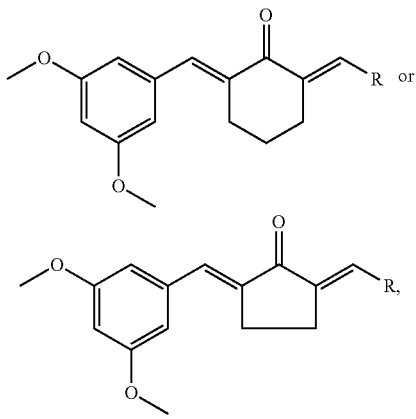

wherein R is selected from aryl or alkyl group.

4. The preparation method according to claim 3, wherein said cyclic ketone is selected from cyclohexanone or cyclopentanone.

5. An antitumor agent, wherein it comprises α-(3,5-dimethoxybenzylidene)-α'-hydrocarbyl methylene cyclic ketone or its medically acceptable salt and pharmaceutically acceptable carriers.

6. The antitumor agent according to claim 5, wherein said α-(3,5-dimethoxybenzylidene)-α'-hydrocarbyl methylene cyclic ketone accounts for 0.05 to 90% by weight of the anti-tumor agent.

7. The antitumor agent according to claim 6, wherein said α-(3,5-dimethoxybenzylidene)-α'-hydrocarbyl methylene cyclic ketone accounts for 15-60% by weight of the anti-tumor agent.

8. The antitumor agent according to claim 5, wherein said carriers comprises solvent, diluent, tablet, capsule, dispersible powder, or granule.

* * * * *